United States Patent [19]
Dubin et al.

[11] Patent Number: 5,834,271
[45] Date of Patent: Nov. 10, 1998

[54] ENZYME-POLYELECTROLYTE COACERVATE COMPLEX AND METHOD OF USE

[75] Inventors: Paul L. Dubin; Barry B. Muhoberac; Jiulin Xia, all of Indianapolis, Ind.

[73] Assignee: Advanced Research and Technology Institute, Inc., Bloomington, Ind.

[21] Appl. No.: 263,041

[22] Filed: Jun. 21, 1994

[51] Int. Cl.$^6$ .................................................. C12N 11/04
[52] U.S. Cl. .............................................................. 435/174
[58] Field of Search ............................................ 435/174

[56] References Cited

U.S. PATENT DOCUMENTS

| | | | |
|---|---|---|---|
| 4,038,485 | 7/1977 | Johnston et al. | 23/230 B |
| 4,431,428 | 2/1984 | Schmer | 604/897 |
| 4,963,367 | 10/1990 | Ecanow | 424/485 |
| 5,324,445 | 6/1994 | Langley et al. | 252/174.12 |

OTHER PUBLICATIONS

Patrickios et al. (1994) ACS Symposium Series, 548, "Interaction of Proteins with Acrylic Polyampholytes", pp. 257–267.

Liebl et al. (1975) "Polymerizations and Similar Reactions of ADP Catalyzed by Polynucleotide Plosphorylase of Proteinoids in Microsystems", in *Proceed. IUB Symp. Prot. Struct. Evol.*, Ed., Fox et al., Dekker, New York, pp. 223–232.

Park et al. (1992) *Macromolecules, 25(1)*, "Effects of Protein Charge Heterogeneity in Protein–Polyelectrolyte Complexation", pp. 290–295.

Xia et al. (1993) *J. Phys. Chem., 97(17)*, "Electrophoretic and Quasi–Elastic Light Scattering of Soluble Protein–Polyelectrolyte Complexes", pp. 4528–4534.

*Primary Examiner*—Jon P. Weber
*Attorney, Agent, or Firm*—Leydig, Voit & Mayer, Ltd.

[57] ABSTRACT

Described are unique preferred enzyme coacervate compositions and their use in catalyzing the reaction of substrates to which the enzyme is specific. Preferred coacervates of the invention are complex coacervates formed by complexing enzymes with polyelectrolytes.

28 Claims, 5 Drawing Sheets

ENZYME-POLYELECTROLYTE COACERVATE COMPLEX AND METHOD OF USE

This invention was made with government support under National Science Foundation Grant No. DMR9014945. The government has certain rights in this invention.

BACKGROUND OF THE INVENTION

The present invention relates generally to enzymes and enzymatic processes, and more particularly to unique coacervates containing enzymes and the use of those coacervates in enzyme-catalyzed reactions.

As further background, enzymes are potentially among the most useful of materials and are capable of catalyzing almost any type of chemical reaction with extraordinary specificity and efficacy. As such, there has been and continues to be tremendous interest in developing techniques for utilizing enzymes in industrial-scale chemical synthesis. While many advances have been made, efforts have been hindered by the general properties characteristic of enzymes and the impact of the techniques employed upon the efficacy of the enzymes.

For example, as proteins, enzymes are fairly sensitive to their environment. Enzymes are highly susceptible to denaturation by chemical or physical factors such as pH extremes, temperature, and/or the presence of organic materials, the latter potentially being the precursor or substrate of interest. These drawbacks have frustrated the use of unstabilized enzymes in solution and have in many instances necessitated the use of large amounts of valuable enzyme over those theoretically required for catalytic activity. The use of such large amounts of catalyst is undesirable in any reaction, as catalysts are generally expensive and some catalyst loss is expected for most processes. However, in the case of enzymes, the disadvantage of their use in large amounts is particularly acute not only because they are highly susceptible to denaturation but also because they are difficult to recover.

In this regard, efforts have been made to improve the recoverability of enzymes by immobilizing them on solid supports, a technique that usually covalently modifies the enzyme and often results in its destabilization and loss of enzymatic activity. Additionally, many methods of immobilization are complex and add significantly to the cost of the catalyst.

In light of the background in this area, there remains a need and demand for improved techniques for utilizing enzymes to catalyze reactions. Preferably, such techniques would overcome many of the difficulties of prior techniques such as enzyme stability and recovery problems, as well as activity losses resulting from immobilization. The present invention addresses these needs.

SUMMARY OF THE INVENTION

Accordingly, in one preferred embodiment the present invention provides an enzymatic process which involves reacting an enzyme substrate in the presence of a coacervate comprised of a polyelectrolyte complexed with an enzyme specific for the substrate. In accordance with the invention, the enzyme and its substrate may be selected from any of the wide variety of known enzymes and substrates. The coacervate will contain the enzyme in an amount effective for catalysis of the reaction at hand, and will also contain a polyelectrolyte which complexes and forms a protective coacervate with the enzyme. Generally, the coacervating agent will be a natural or synthetic macromolecule (polymer) which has the capacity to form a coacervate when combined with the enzyme. Typically, an enzyme can be combined with a macromolecule having the opposite charge to form a coacervate. The coacervate, which also forms a part of the present invention, can be used in a number of processing modes including both batchwise and continuous modes, and can be freely dispersed in the reaction medium or used in supported forms such as in membrane-assisted processing technology.

Another preferred embodiment of the invention provides a process for preparing an enzyme composition for catalyzing reaction of a substrate to the enzyme. This process involves the formation of a complex coacervate comprised of an enzyme complexed with a polyelectrolyte, said complex coacervate being a separate dispersed phase, but yet permeable to said substrate.

As to advantages, in the present invention the incorporation of the enzyme in a coacervate improves its stability with respect to temperature and pH as compared to corresponding non-incorporated enzymes. In addition, the coacervated enzymes are expected to be more stable in mixed aqueous-organic media such as water in mixture with water-miscible organic solvents such as alcohols, ethers and the like such as would expand the number of utilizable substrates to include those not water soluble. Moreover, the enzymes can be effectively recovered by recovering the coacervates containing them. The enzyme coacervates of the invention can provide highly unexpected increases in rates of reaction, for example where the substrate is more soluble in the coacervate than in the surrounding media. In such instances, high concentrations of the substrate in the coacervate are achieved thus providing increased rates of reaction. Further, the coacervates of the invention can be used in a number of reaction modes and can be adsorbed onto other materials such as filters or membranes, to reversibly immobilize the enzyme.

These and additional features, objects and advantages of the invention will be apparent from the following description.

DESCRIPTION OF THE PREFERRED EMBODIMENT

Figure 1:
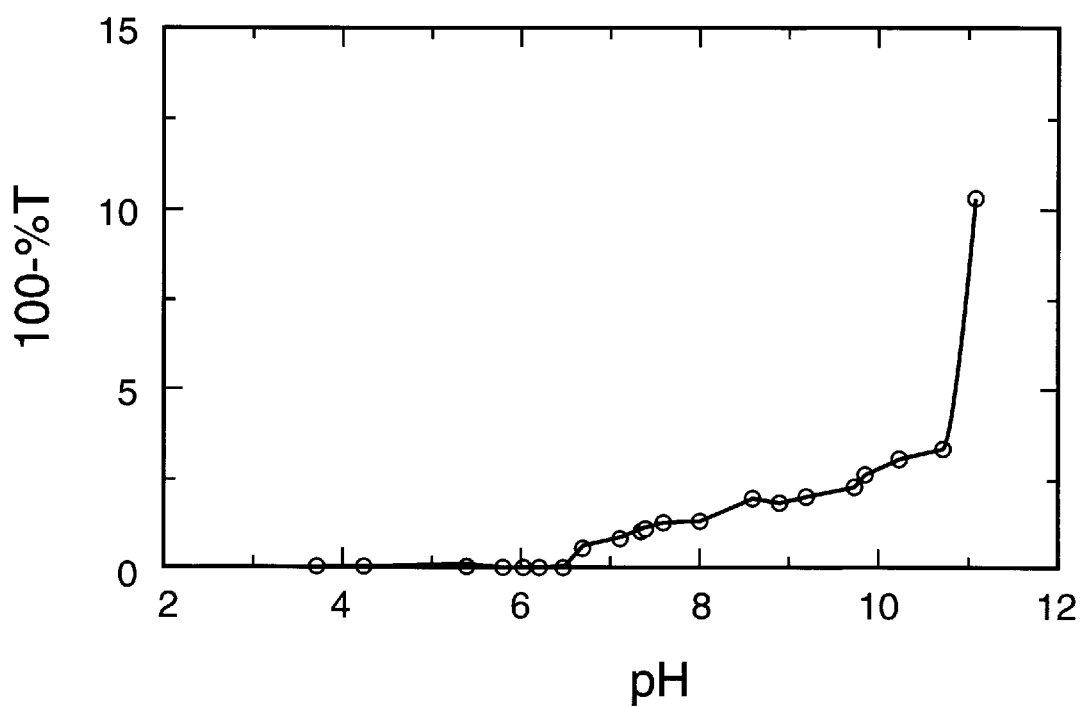
FIG. 1 provides a "Type 1" turbidimetric titration curve demonstrating the formation of an inventive coacervate, as further described in Example 1, infra.

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention pertains.

As indicated above, preferred embodiments of the invention relate to enzyme coacervates and preparations and uses thereof. The coacervates of the invention are aggregates of colloidal droplets arising via aggregation primarily through the force of electrostatic attraction. In accordance with the present invention, the coacervates advantageously incorporate the enzyme in a fashion which increases its stability in regard to the effects of the surrounding environment, while being permeable to the substrate so as to allow the enzyme-substrate interaction and reaction.

Preferred coacervates for use in the invention are formed at least in part by the complexation of the enzyme itself with a polyelectrolyte. That is, the enzyme will itself be an active coacervating agent rather than simply a substance incorporated in a coacervate otherwise formed by other materials. Thus, preferred coacervates will be "complex coacervates". As is known, complex coacervates are formed when hydrophilic materials are caused to emerge from solution by being complexed with another hydrophilic material which process decreases the collective solubilities of the materials in the solution. Thus, generally, the emergent phase includes the predominant portion of both hydrophilic materials. In contrast, in simple coacervation, a single kind of hydrophilic material is caused to emerge from solution by the addition of a phase-separation-inducing substance. The emergent phase then contains a relatively high concentration of the hydrophilic material and the phase-separation inducing substance is substantially evenly distributed between the emergent phase and the remaining continuous phase.

In accordance with the present invention, the emergent or "colloid" phase of the coacervate will contain sufficient amounts of the enzyme to catalyze the desired reaction. Typically, the colloid phase will be substantially comprised of enzyme, for example containing at least about 0.1 weight percent of enzyme, more typically in the range of about 0.1 to 5 weight percent of enzyme. In any case, it is generally preferred to use at least a slight excess of the polyelectrolyte relative to the enzyme, to avoid enzyme losses.

Preferred coacervates of the invention can be prepared by forming a coacervate in an aqueous or other medium by interaction of an enzyme and a polyelectrolyte which exhibit net charges opposite from one another. In this regard, it is well known that enzymes typically carry a net charge in their naturally occurring forms; however, in accordance with the invention, enzymes may also contain modified amino acids or amino acid sequences which alter the net charge characteristics of the enzyme to modify the coacervation process. Thus, both naturally-occurring and modified enzymes may be employed in the invention. In addition, the polyelectrolyte may be designed so that hydrophobic interactions with the enzyme enhance or modulate coacervate formation and the properties thereof, thus extending the utility of the invention to include enzymes extracted from biological membranes.

To form the coacervate, the polyelectrolyte and enzyme can be added separately or together in an aqueous medium or other suitable medium for forming the coacervate. Of course, the medium should be non-denaturing to the enzyme being utilized. As to medium parameters, several factors such as temperature, pH, polarity and ionic strength of the medium will affect the formation of the coacervate. Given the disclosure herein, the selection and control of these parameters in order to form coacervates in accordance with the invention will be well within the abilities of the skilled artisan. The particular temperature at which the coacervate is formed is not critical; however, the temperature will of course be selected so as to avoid substantial degradation of the enzyme. Ambient temperatures (e.g. 20° to 25° C.) are convenient and can be utilized in the present invention.

As indicated previously, there are a great number of enzymes which are well-known and which can be used in the present invention, and the particular enzyme employed is not a limiting factor, inasmuch as the choice of polymer and pH can be appropriately adjusted to suit a particular enzyme. Representative enzymes utilizable in the invention include for example urease, alpha amylase, lipase, trypsin, asparaginase, α-chymotrypsin, 1,4-α-D-glucosidase, glucoamylase, lactate dehydrogenase, alcohol dehydrogenase, penicillin amidase, β-D-galactosidase, glucose-6-phosphate dehydrogenase, and the like. These and other enzymes are well-known to the skilled artisan and will be used in the present invention alone or in advantageous combination with one or more other enzymes (e.g. the use of two enzymes which sequentially act upon an initial substrate or which act on separate substrates) without any undue burden.

Preferred polyelectrolytes for use in the invention will be macromolecules that carry a net charge opposite to that of the enzyme to be coacervated. These may include both synthetic and natural products including, for example, synthetic polymers containing carboxyl groups such as poly (acrylic acid) and poly(alkyl acrylic acids), e.g. poly (methacrylic acid); polymers containing quaternary salt groups, including heterocyclic quaternary salt groups such as quaternized pyridinyl groups, e.g. those found in quaternized poly(vinylpyridine) polymers, as well as polymers including aliphatic quaternary salt groups; polymers containing ammonium salt groups such as poly (dimethyldiallylammoniumchloride) ("PDMADAAC"); and polymers containing sulfonate groups such as those found in sodium poly(styrenesulfonate). These and other polyelectrolytes, including those similar to the aforementioned but incorporating selected hydrophobic moieties, which form a coacervate upon complexing with the enzyme will be suitable and their use in the invention will be well within the purview of those skilled in the art.

Coacervates of the invention can be used in a wide variety of processing and reaction schemes and can be formed in situ or prior to use. For example, the coacervates can be dispersed within a bulk reaction vessel along with the substrate for the coacervated enzyme and any necessary cofactors or other reactants. Typically, the reaction solvent for such reactions will be aqueous and may be water only or may contain a mixture of water and a water-miscible organic solvent. Representative organic solvents include, for example, polar organic solvents such as alcohols, especially lower alcohols such as $C_1$ to $C_5$ alcohols, e.g. methanol, ethanol, n-propanol, isopropanol, n-butanol, iso-butanol, tert-butanol, pentanol, and the like; ethers, including cyclic ethers such as dioxane; or other polar solvents such as acetonitrile. The reaction solvent employed will of course vary in accordance with many factors including the particular enzyme/substrate combination being used and the polarity of the substrates.

In addition to being employed in bulk reactions, the enzyme coacervates of the invention can also be utilized in membrane-assisted synthesis. In such cases, the enzyme/ polymer coacervate can be adsorbed onto a membrane in any desirable form including sheet or hollow fiber forms, so as to be loaded onto one side of the membrane. Substrate can then be contacted with the enzyme coacervate to react to form a product selectively permeable through the membrane, thus passing through the membrane for effective recovery on the opposed side. This reaction scheme can provide highly effective use of enzyme coacervates while simplifying procedures for product recovery and workups. Enzyme coacervates of the invention can also be adsorbed onto other solid support materials including particulate or bead-form materials, while retaining many other advantages afforded by the enzyme coacervate system as discussed above.

Products formed by reactions of the invention can be conventionally recovered and utilized. Likewise, coacervates of the invention can be recovered for reuse using conventional techniques such as centrifugation, or, where membrane-assisted or supported forms of the coacervates are employed, the membrane or support loaded with the coacervate can be recovered for reuse.

In order to promote a further understanding and appreciation of the present invention and its attendant advantages, the following specific Examples are provided. It will be understood that these Examples are illustrative and not limiting in nature.

EXAMPLE 1

Preparation of Alcohol Dehydrogenase (ADH)-PDMDAAC Complexes

In this Example, a complex coacervate was formed by complexing horse liver ADH (MW 80,000; IEP 6.8) with PDMDAAC in aqueous medium. The enzyme and polyelectrolyte were added to a 0.01M aqueous NaCl solution. The pH of the solution was then increased by the addition of NaOH to form the complex coacervate.

In particular, FIG. 1 shows a "Type 1" turbidimetric titration curve of PDMDAAC at a concentration of 0.1 g/L in 0.05 g/L ADH solution, at ionic strength (I) of 0.01M NaCl. As can be seen, The titration curve displays an abrupt increase in turbidity at pH 11, corresponding to colloidal complex formation. Prior to colloid formation, a small turbidity increase at pH 6.8 was observed. This small turbidity increase is believed to be due to the initial formation of a soluble complex. It is noteworthy that the complex particles formed at pH 11 at this I were very stable. The size of the particle measured by quasi-elastic light scattering (QELS) in 0.01M phosphate pH 11 buffer solution was about 400 nm in diameter. The mobility of the particle under the same condition was 1.5 $\mu$m-cm/V-s.

EXAMPLE 2

Use of Coacervate

ADH catalyzes the following reaction:

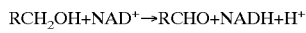

$RCH_2OH + NAD^+ \rightarrow RCHO + NADH + H^+$

Figure 2:
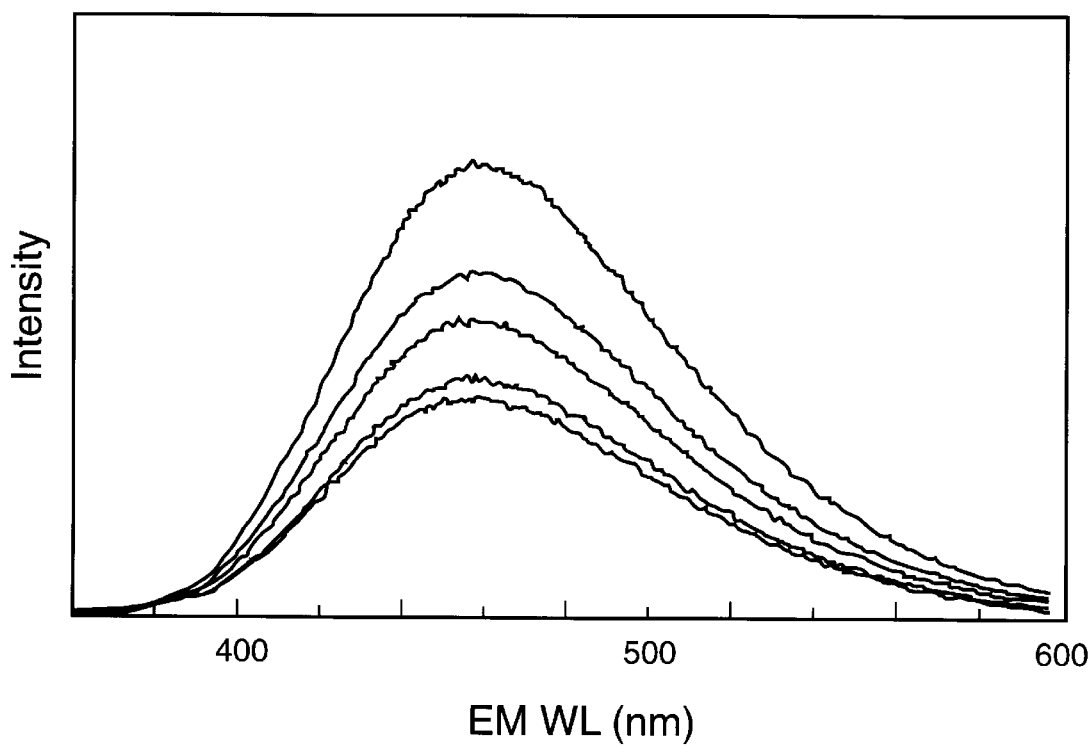
FIG. 2 shows fluorescence emission spectra tracking the formation of NADH during the conversion of methanol to formaldehyde in the presence of coacervated alcohol dehydrogenase (ADH), as further described in Example 2, infra.

In order to use the ADH-PDMDAAC complex as an enzymatic micro-reactor for the above reaction, a stable complex formed in 0.01M and pH 11 phosphate buffer was used. FIG. 2 shows fluorescence emission spectra of NADH, obtained at different times after mixing the complex with 0.002M $NAD^+$ and 0.16M $CH_3OH$ in 0.01M and pH 11 phosphate buffer. Complete mixing was assured by vortexing the solution for 20 seconds. The concentrations of ADH and PDMDAAC were 0.06 and 0.12 g/L, respectively. The increase of the emission intensity at 450 nm with time is due to the formation of NADH. Therefore, the bound ADH in the complex remains active for catalysis of the above reaction. In the fluorescence measurement, a triangular cell was used to penetrate the turbid solution.

Figure 3:
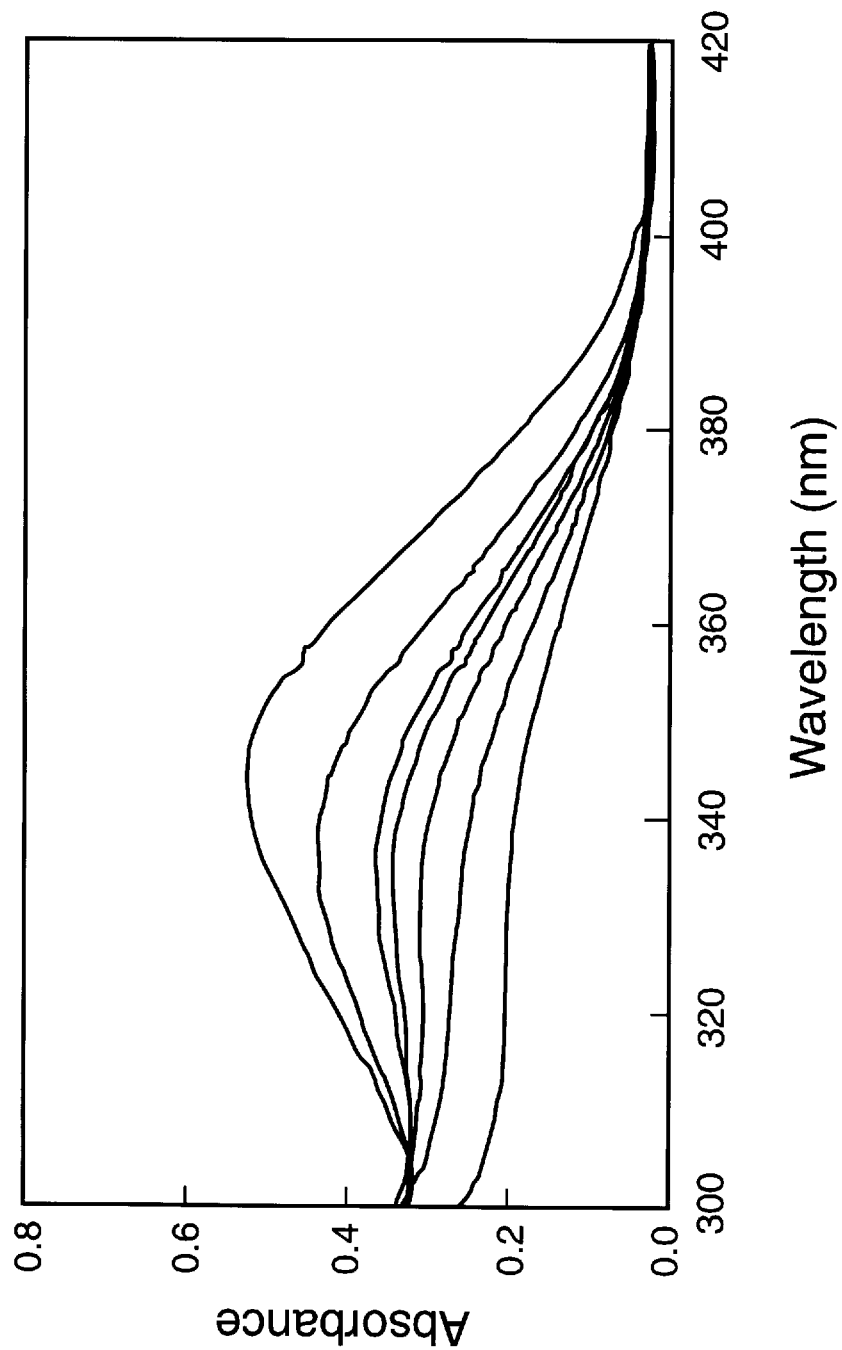
FIG. 3 shows UV absorbance spectra for samples periodically taken from a coacervated-ADH/MeOH/NAD$^+$ reaction medium, which demonstrate changing absorbance with time and so evidence formation of NADH over time.
Figure 4:
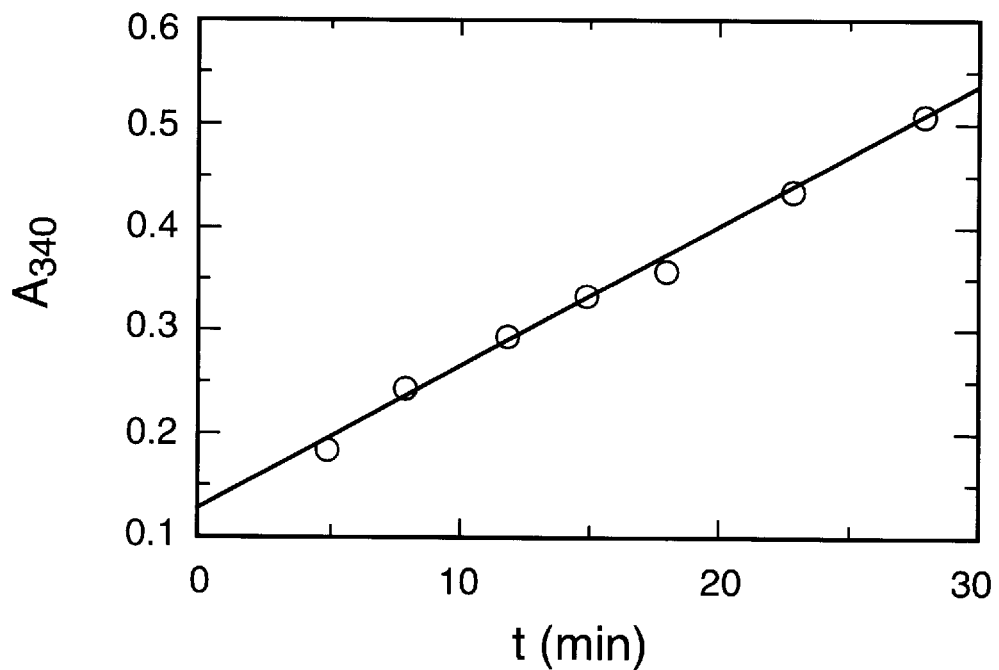
FIG. 4 shows a plot of absorbance at 340 nm verses time for a coacervated-ADH/MeOH/NAD$^+$ reaction medium, demonstrating the rate of NADH formation.
Figure 5:
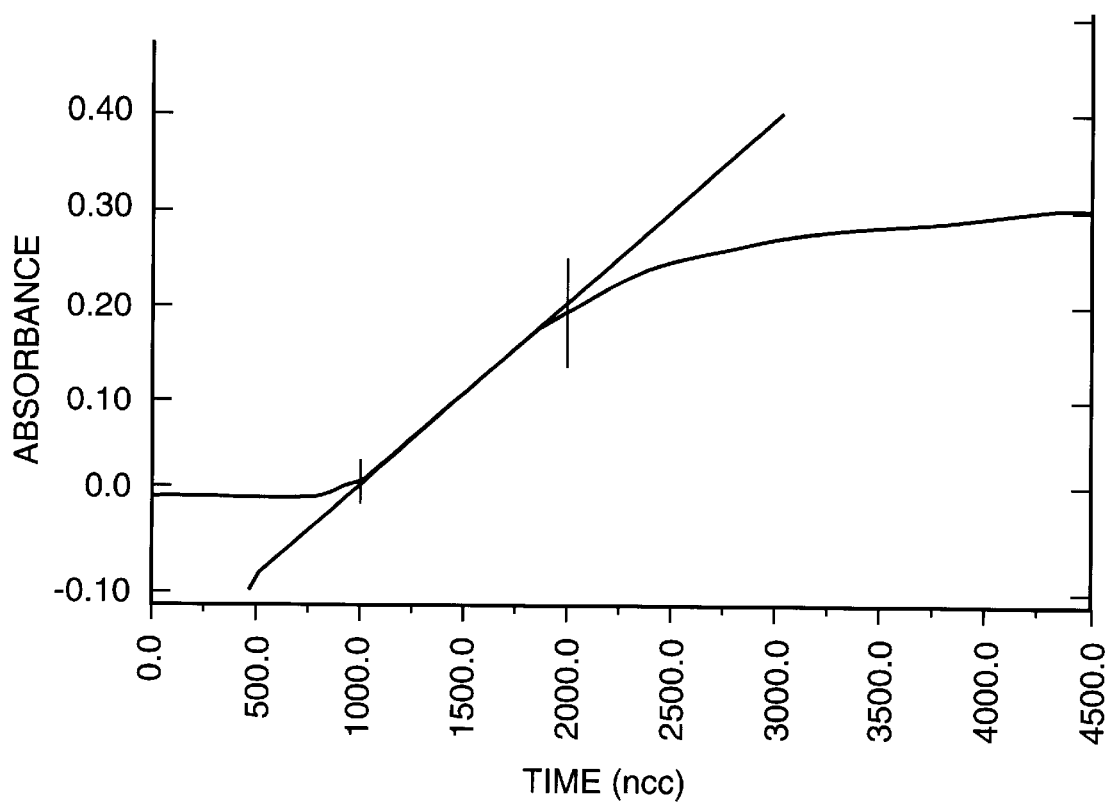
FIG. 5 is a plot showing the rate of NADH formation by a reaction medium initially containing non-coacervated ADH, MeOH and NAD$^+$.

In order to measure the enzyme activity of the ADH-PDMDAAC complex for the above reaction, the NADH concentration was measured by UV-visible spectrometry at 340 nm. The complex was first formed at concentrations of 0.06 g/L ADH and 0.12 g/L PDMDAAC in 0.01M pH 11 phosphate buffer solution. The complex was then mixed with 0.002M NAD and 0.16M $CH_3OH$ by vortexing 20 seconds, in the same buffer solution. After vortexing, the solution was stirred by a magnetic stirrer. The solution was sampled at different times. For each sampling, a 1 ml solution was taken and filtered into a UV spectrophotometer cell through a 0.2 $\mu$m filter. The solution obtained was diluted by adding the same amount of buffer to the cell before the measurement of absorbance. FIG. 3 shows the absorbance spectra obtained at times of 5, 8, 12, 15, 18, 23 and 28 minutes after mixing the complex and the substrates. FIG. 4 is the plot of the absorbance at 340 nm vs time. From the slope of the linear plot, the enzyme activity of 0.075 units/mg ADH was measured. This activity is about two times larger than that of the pure (polyelectrolyte-free) ADH at the same conditions. The activity measurement for the pure ADH was carried out by monitoring $A_{340}$ as function of time (FIG. 5).

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. An enzymatic process comprising the steps of:
   first, forming a stable polyelectrolyte-enzyme coacervate dispersed as liquid droplets in a continuous liquid medium by mixing the polyelectrolyte with at least one enzyme so that the at least one enzyme is confined within the coacervate liquid droplets throughout the enzymatic process;
   second, introducing a substrate into solution in the continuous liquid medium to react with the at least one enzyme to form a product, the substrate moving from the continuous liquid medium into the liquid droplets and the product moving from the liquid droplets into the continuous liquid medium; and thereafter
   harvesting the product from the continuous liquid medium; and
   recovering the stable, liquid polyelectrolyte-enzyme coacervate for reuse.

2. An enzymatic process as defined in claim 1, wherein the continuous liquid medium comprises water.

3. A process as defined in claim 1, wherein the at least one enzyme comprises at least about 0.1 percent by weight of the coacervate.

4. A process as defined in claim 3, wherein the at least one enzyme comprises about 0.1 to abut 5 percent by weight of the coacervate.

5. A process as defined in claim 1, wherein the polyelectrolyte is a synthetic polymer.

6. A process as defined in claim 5, wherein the polyelectrolyte is selected from the group consisting of poly(acrylic acid) poly(alkyl acrylic acids), quaternized poly (vinylpyridines), poly(dialkyldiallylammoniumchlorides), and sodium poly(styrenesulfonate).

7. A process as defined in claim 1, wherein the coacervate comprises a plurality of enzymes.

8. An enzymatic process comprising the steps of:

forming a stable polyelectrolyte-enzyme liquid coacervate mixture by mixing the polyelectrolyte with at least one enzyme;

dispersing the polyelectrolyte-enzyme mixture as liquid coacervate droplets within a continuous liquid medium so that the at least one enzyme is confined within the liquid droplets throughout the enzymatic process;

introducing a substrate into solution in the continuous liquid medium to react with the at least one enzyme to form a product, the substrate moving from the continuous liquid medium into the liquid coacervate droplets and the product moving from the liquid coacervate droplets into the continuous liquid medium; and thereafter harvesting the product from the continuous liquid medium; and recovering the stable, liquid polyelectrolyte-enzyme coacervate mixture for reuse.

9. A process as defined in claim 8, wherein the continuous liquid medium comprises water.

10. A process as defined in claim 8, wherein the at least one enzyme comprises at least about 0.1 percent by weight of the polyelectrolyte-enzyme coacervate mixture.

11. A process as defined in claim 10, wherein the at least one enzyme comprises about 0.1 to about 5 percent by weight of the polyelectrolyte-enzyme coacervate mixture.

12. A process as defined in claim 8, wherein the polyelectrolyte is a synthetic polymer.

13. A process as defined in claim 12, wherein the polyelectrolyte is selected from the group consisting of poly (acrylic acid), poly(alkyl acrylic acids), quaternized poly (vinylpyridines), poly(dialkyldiallylammoniumchlorides), and sodium poly(styrenesulfonate).

14. A process as defined in claim 8, wherein the coacervate comprises a plurality of enzymes.

15. An enzymatic process, comprising:

forming a reaction mass by charging to a reactor (i) a stable, polyelectrolyte-enzyme coacervate dispersed as liquid droplets in a continuous liquid medium by mixing the polyelectrolyte with at least one enzyme so that the at least one enzyme is confined within the liquid droplets throughout the enzymatic process, and (ii) a substrate, for which the at least one enzyme is specific, in solution in the continuous phase;

maintaining the reaction mass under conditions in which the at least one enzyme catalyzes reaction of the substrate to form a product while the at least one enzyme is incorporated in the coacervate liquid droplets; and thereafter harvesting the product from the continuous liquid medium; and recovering the stable, liquid polyelectrolyte-enzyme coacervate for reuse.

16. A process as defined in claim 15, wherein the at least one enzyme comprises at least about 0.1 percent by weight of the coacervate.

17. A process as defined in claim 16, wherein the at least one enzyme comprises about 0.1 to about 5 percent by weight of the coacervate.

18. A process as defined in claim 15, wherein the polyelectrolyte is a synthetic polymer.

19. A process as defined in claim 18, wherein the polyelectrolyte is selected from the group consisting of poly (acrylic acid), poly(alkyl acrylic acids), quaternized poly (vinylpyridines), poly(dialkyldiallylammoniumchlorides), and sodium poly(styrenesulfonate).

20. A process as defined in claim 15, wherein the coacervate comprises a plurality of enzymes.

21. A process as defined in claim 15, wherein the coacervate is formed in situ in said reactor.

22. A composition comprising:

stable polyelectrolyte-enzyme coacervate dispersed as liquid droplets in a continuous liquid medium formed by mixing the polyelectrolyte with at least one enzyme so that the at least one enzyme is confined within the liquid droplets; and a substrate which is soluble in the continuous phase, the coacervate being permeable to the substrate for which the at least one enzyme is specific.

23. A composition as defined in claim 22, wherein the at least one enzyme comprises at least about 0.1 percent by weight of the coacervate.

24. A composition as defined in claim 23, wherein the at least one enzyme comprises about 0.1 to about 5 percent by weight of the coacervate.

25. A composition as defined in claim 22, wherein the polyelectrolyte is a synthetic polymer.

26. A composition as defined in claim 25, wherein the polyelectrolyte is selected from the group consisting of poly(acrylic acid), poly(alkyl acrylic acids), quaternized poly(vinylpyridines), poly(dialkyldiallylammoniumchlorides), and sodium poly(styrenesulfonate).

27. A composition as defined in claim 26, wherein the at least one enzyme comprises at least about 0.1 percent by weight of the coacervate.

28. A composition as defined in claim 22, wherein the coacervate comprises a plurality of enzymes.

* * * * *